(12) United States Patent
Simons

(10) Patent No.: US 7,695,433 B2
(45) Date of Patent: Apr. 13, 2010

(54) LARYNGOSCOPE WITH DISPOSABLE BLADE COVER

(75) Inventor: Jonathan Simons, Savannah, GA (US)

(73) Assignee: Zeppelin Designs, Inc., Saint Simons Island, GA (US)

( * ) Notice: Subject to any disclaimer, the term of this patent is extended or adjusted under 35 U.S.C. 154(b) by 316 days.

(21) Appl. No.: 11/657,876

(22) Filed: Jan. 24, 2007

(65) Prior Publication Data

US 2008/0177147 A1   Jul. 24, 2008

(51) Int. Cl.
 *A61B 1/267* (2006.01)
 *A61B 1/32* (2006.01)
(52) U.S. Cl. ............... 600/186; 600/185; 600/190; 600/193; 600/203
(58) Field of Classification Search ............... 600/121, 600/124, 125, 185, 186, 203
 See application file for complete search history.

(56) References Cited

U.S. PATENT DOCUMENTS

| | | | |
|---|---|---|---|
| 3,426,749 A | 2/1969 | Jephcott | |
| 3,595,222 A | 7/1971 | Vellacott | |
| 3,598,113 A | 8/1971 | Moore | |
| 3,766,909 A | 10/1973 | Ozbey | |
| 3,943,920 A | 3/1976 | Kandel | |
| 4,112,933 A | 9/1978 | Moses | |
| 4,114,609 A | 9/1978 | Moses | |
| 4,295,465 A | 10/1981 | Racz | |
| 4,306,547 A | 12/1981 | Lowell | |
| 4,360,008 A | 11/1982 | Corazzelli, Jr. | |
| 4,406,280 A | 9/1983 | Upsher | |
| 4,437,458 A | 3/1984 | Upsher | |
| 4,527,553 A | 7/1985 | Upsher | |
| 4,546,762 A | 10/1985 | Upsher | |
| 4,565,187 A | 1/1986 | Soloway | |
| 4,579,108 A | 4/1986 | Bauman | |
| 4,583,527 A | 4/1986 | Musicant et al. | |
| 4,611,579 A | 9/1986 | Bellhouse | |
| 4,807,600 A | 2/1989 | Hayes | |
| 4,834,077 A | 5/1989 | Sun | |
| 4,878,486 A | 11/1989 | Slater | |
| 4,884,558 A | 12/1989 | Gorski et al. | |
| 4,930,495 A | 6/1990 | Upsher | |
| 4,972,825 A | 11/1990 | Vescovo, Jr. | |
| 4,979,499 A | 12/1990 | Sun | |
| 5,003,962 A | 4/1991 | Choi | |
| 5,063,907 A | 11/1991 | Musicant | |
| 5,065,738 A | 11/1991 | Van Dam | |
| 5,184,603 A | 2/1993 | Stone | |
| 5,263,472 A | 11/1993 | Ough | |
| 5,277,173 A | 1/1994 | Cantele | |
| 5,329,937 A | 7/1994 | Krstevich et al. | |
| 5,347,995 A | 9/1994 | Slater et al. | |
| 5,355,870 A | 10/1994 | Lacy | |
| 5,406,941 A | 4/1995 | Roberts | |
| 5,425,356 A | 6/1995 | Ough | |
| 5,443,058 A | 8/1995 | Ough | |
| 5,498,231 A | 3/1996 | Franicevic | |
| 5,536,245 A | 7/1996 | Dahlbeck | |

(Continued)

*Primary Examiner*—Thomas C Barrett
*Assistant Examiner*—Christian Sevilla
(74) *Attorney, Agent, or Firm*—Jacqueline Hutter

(57) ABSTRACT

A laryngoscope for use with a disposable blade cover is provided. The laryngoscope comprises a handle and a blade. The laryngoscope further comprises an actuator system for selectively securing the disposable blade cover about at least a portion of the blade.

16 Claims, 8 Drawing Sheets

U.S. PATENT DOCUMENTS

| | | |
|---|---|---|
| 5,542,905 A | 8/1996 | Nussenbaum |
| 5,603,688 A | 2/1997 | Upsher |
| 5,651,760 A * | 7/1997 | Upsher .............. 600/193 |
| 5,702,351 A | 12/1997 | Bar-Or |
| 5,743,849 A * | 4/1998 | Rice et al. ............ 600/186 |
| 5,772,581 A | 6/1998 | Gaines |
| 5,776,053 A | 7/1998 | Dragisic |
| 5,819,727 A | 10/1998 | Linder |
| 5,879,304 A | 3/1999 | Shuchman |
| 6,001,066 A * | 12/1999 | Canfield et al. ............ 600/559 |
| 6,013,026 A | 1/2000 | Krauter |
| 6,036,639 A | 3/2000 | Allred, III |
| 6,102,851 A | 8/2000 | Mellin |
| 6,213,937 B1 | 4/2001 | Vivenzio |
| 6,217,514 B1 | 4/2001 | Gruen |
| 6,248,061 B1 | 6/2001 | Cook, Jr. |
| 6,277,068 B1 | 8/2001 | Wojnowicz |
| 6,354,993 B1 | 3/2002 | Kaplan |
| 6,494,828 B1 | 12/2002 | Berall |
| 6,623,425 B2 | 9/2003 | Cartledge |
| 6,719,688 B2 | 4/2004 | Pecherer |
| 6,991,604 B2 | 1/2006 | Cantrell |
| 7,044,909 B2 | 5/2006 | Berci |
| 7,128,710 B1 * | 10/2006 | Cranton et al. ............ 600/199 |
| 2001/0014768 A1 | 8/2001 | Kaplan |
| 2002/0082477 A1 | 6/2002 | Kim |
| 2003/0098026 A1 | 5/2003 | Saied |
| 2004/0122292 A1 | 6/2004 | Dey |
| 2004/0210115 A1 | 10/2004 | Ma |
| 2004/0220454 A1 | 11/2004 | Dalle |
| 2005/0187434 A1 | 8/2005 | Dey |
| 2005/0192481 A1 | 9/2005 | Berci |
| 2005/0234297 A1 * | 10/2005 | Devierre et al. ............ 600/153 |
| 2005/0240081 A1 | 10/2005 | Eliachar |
| 2006/0074276 A1 | 4/2006 | Cantrell |

* cited by examiner

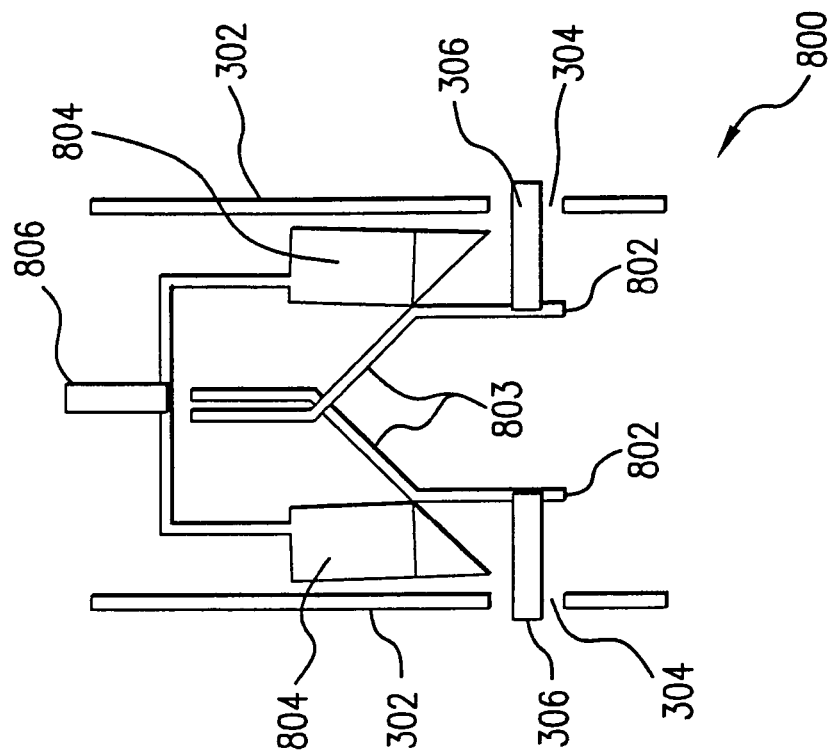
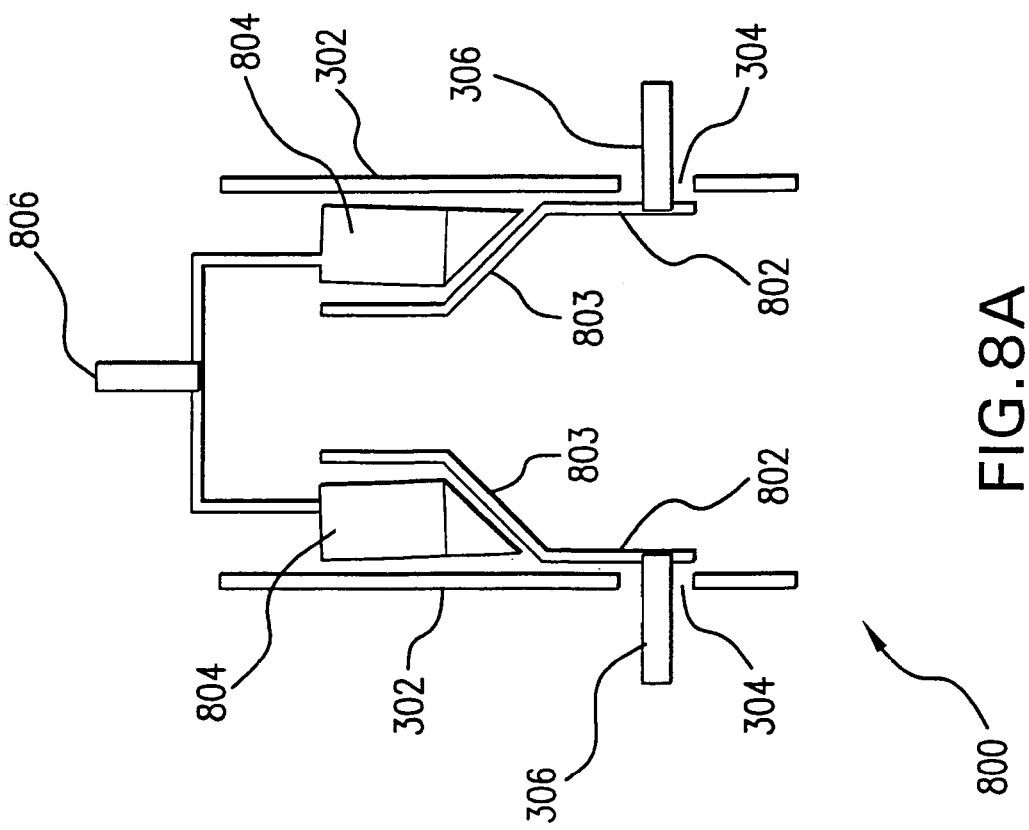

LARYNGOSCOPE WITH DISPOSABLE BLADE COVER

BACKGROUND OF THE INVENTION

Laryngoscopes are common devices used in medical and surgical practice. A laryngoscope generally comprises a blade portion and a handle portion. The primary use of a laryngoscope is to expose the larynx of a patient to assist with the placement of an endotracheal tube. During endotracheal tube placement, laryngoscopes tend to be contaminated by the patient's oral fluids. Contaminated laryngoscopes endanger both medical practitioner and patients. Needed in the art is a convenient system and laryngoscope for use with a disposable blade covering that allows for decreased contamination.

SUMMARY OF THE INVENTION

In accordance with the purpose(s) of this invention, as embodied and broadly described herein, this invention, in one aspect, relates to a laryngoscope for use with a disposable blade cover. The laryngoscope comprises a handle and a blade. The laryngoscope further comprises an actuator system for selectively securing the disposable blade cover about at least a portion of the blade.

BRIEF DESCRIPTION OF THE DRAWINGS

The accompanying drawings, which are incorporated in and constitute a part of this specification, illustrate certain aspects of the instant invention and together with the description, serve to explain, without limitation, the principles of the invention. Like reference characters used therein indicate like parts throughout the drawings.

FIGS. 8A and 8B are schematic illustrations of an exemplary actuator system of the present invention.

DETAILED DESCRIPTION OF THE INVENTION

Figure 1:
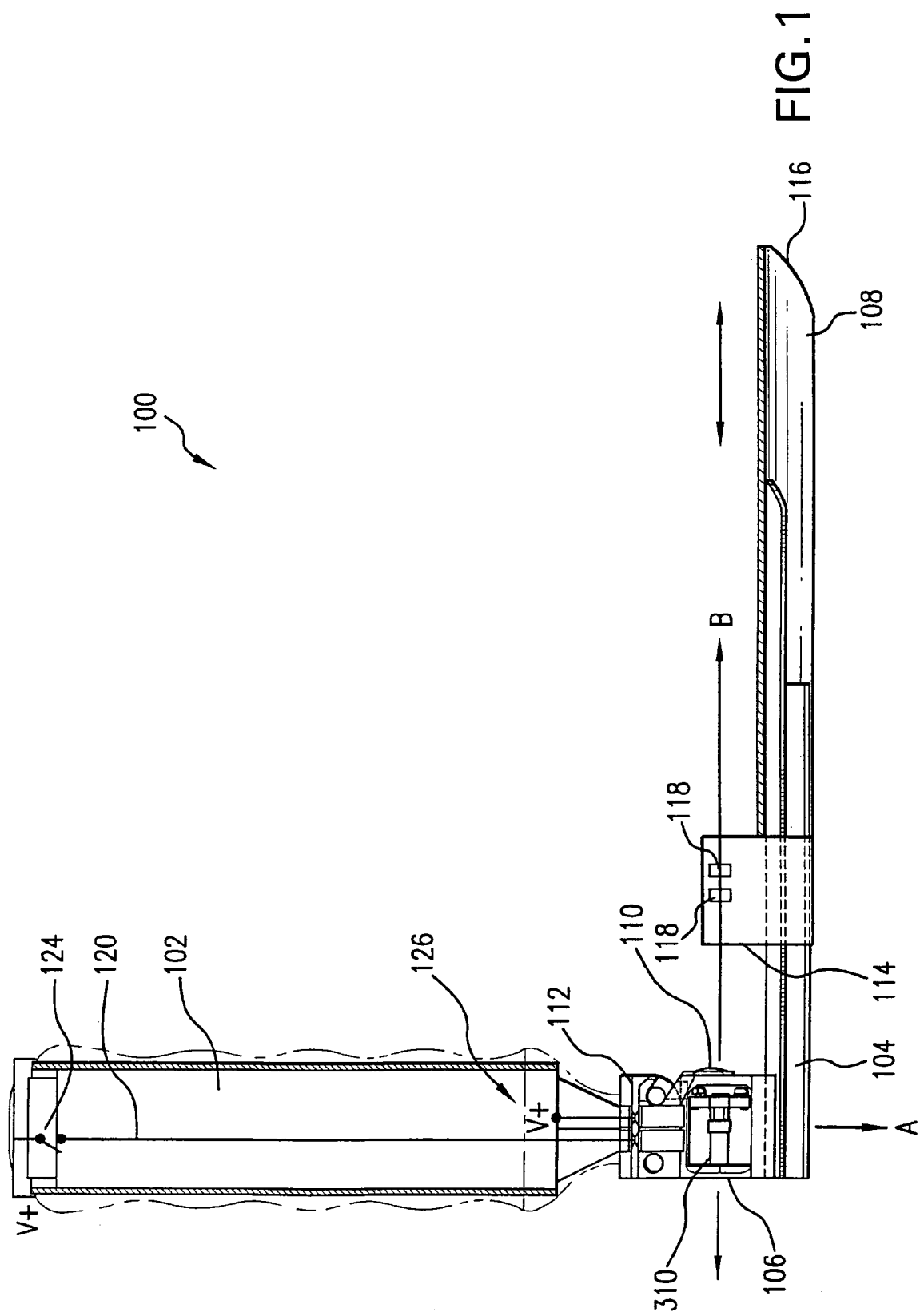
FIG. 1 is a schematic side elevational view of a first embodiment of a laryngoscope and disposable blade cover of the present invention.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "surface" includes aspects having two or more such surfaces unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

By a "subject" is meant an individual. The term subject includes small or laboratory animals as well as primates, including humans. The term subject does not denote a particular age or sex. Thus, adult and newborn animals, whether male or female, are included. The term "patient" includes human and veterinary patients.

The present invention may be understood more readily by reference to the following detailed description of preferred embodiments of the invention and the examples included therein and to the Figures and their previous and following description.

Referring generally to the figures, provided herein is a laryngoscope for use with a disposable blade cover. In one aspect, the laryngoscope comprises a handle and a blade. In a further aspect, the laryngoscope can further comprise an actuator system for selectively securing the disposable blade cover about at least a portion of the blade.

Figure 3:
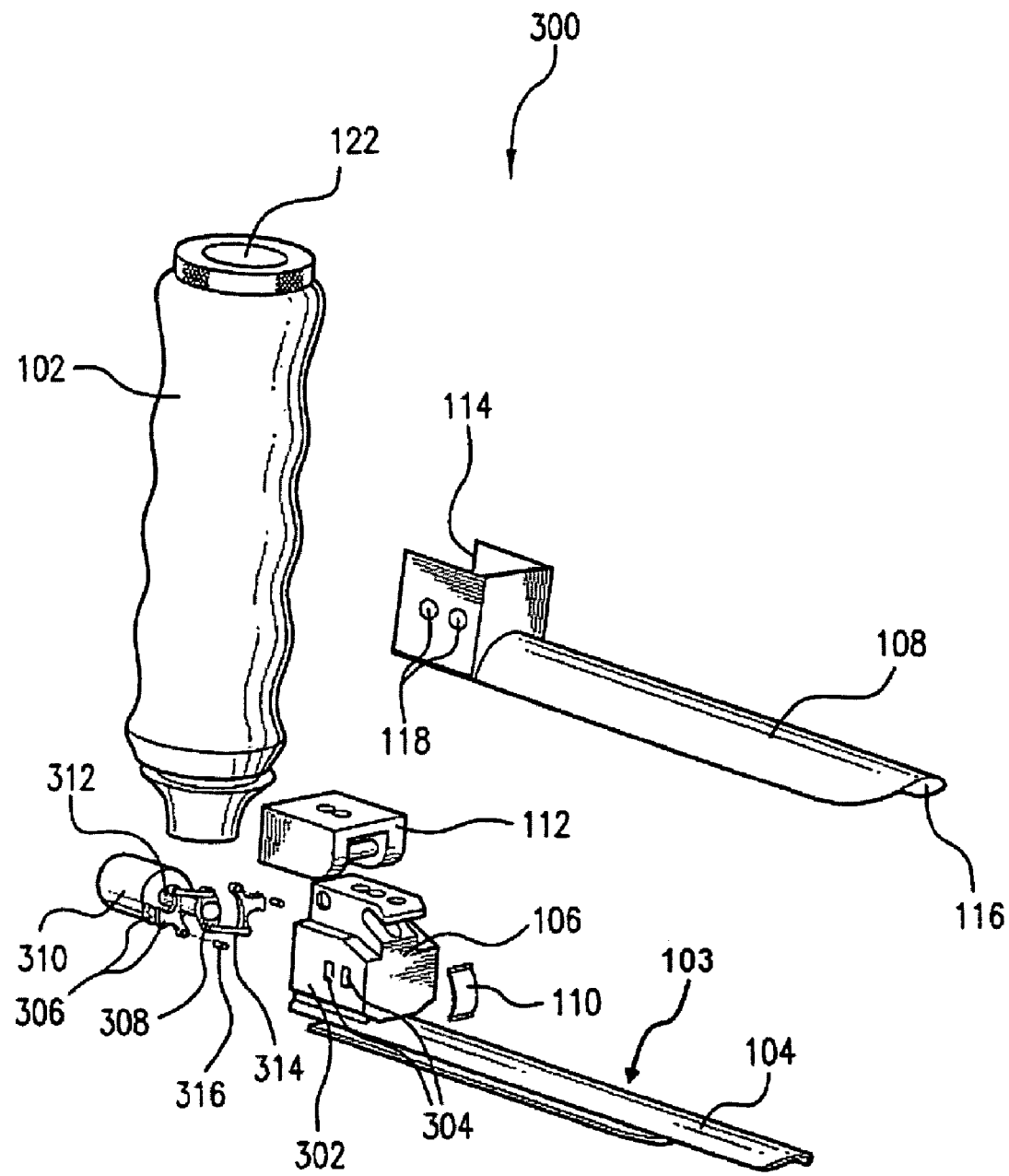
FIG. 3 is an exploded perspective view of the laryngoscope and disposable blade cover of FIG. 1.

Referring to FIGS. 1 and 3, an exemplary laryngoscope in accordance with one embodiment of the disclosed invention is illustrated. In one aspect, the exemplary laryngoscope 100 comprises a handle 102 and a blade 103. In this aspect, the blade 103 comprises an elongated portion 104 and a mounting portion 106. In a further aspect, the mounting portion can be used to mount the blade to a portion of the laryngoscope handle.

It is contemplated that the laryngoscope can be used with a disposable sleeve, cover or sheath 108. One skilled in the art will appreciate that such terms are used interchangeably throughout and are intended to cover any rigid or semi-rigid covering material that can be placed about at least a portion of the elongated blade portion. In another aspect, the disposable sheath 108 can also be designed and used to cover portions of the mounting portion of the blade 106 and/or to cover portions of the handle 102, if desired.

In one aspect, the disposable sheath or sleeve can have a proximal end and a spaced distal end. In this aspect, a portion of the distal end of the disposable sheath defines at least one cavity that is configured to complementarily surround at least a portion of the distal end of the elongated portion of the blade. In another aspect, the disposable sleeve can be used to cover at least a portion of the elongated blade portion during insertion of the blade into the oropharynx of the subject. In this aspect, the disposable sleeve can be configured to protect the blade from contact with the oropharynx or from fluids found therein during operation.

In a further aspect, the disposable sleeve can act to keep the elongated blade portion clean and free of debris by encasing it in a rigid or semi-rigid material which can be selectively slideably removed from the elongated blade portion. It is contemplated that the sleeve can be made of any material known for covering and protecting medical instruments including plastic or other semi-rigid materials.

In various aspects, the disposable sleeve 108 can be configured to be slideably and selectively removed from the laryngoscope. For example, the disposable sleeve can be slideable and selectively removed from the elongated blade portion. Optionally, the disposable sleeve can also be selectively removed from portions of the handle or mounting portion of the blade if portions of the handle or mounting portion of the blade are covered by the disposable sleeve.

In one aspect, the disposable sleeve can be removed by manually sliding the sleeve distally away from the mounting portion of the blade along the longitudinal axis of the elongated portion of the blade 103. It is contemplated that the sleeve can be disposed of once it separated from the blade. A clean disposable sheath 108 can then be positioned over the elongated portion 104 of the blade by sliding the covering proximally along the elongated blade portion towards the mounting portion of the blade and the handle.

It is contemplated that the elongated portion 104 of the blade 103 can vary in length. One skilled in the art will appreciate that the described invention is not intended to be limited by any dimension of the elongated portion of the blade including its length, width, or shape. The elongated blade portion 104, and the laryngoscope as a whole, can be used to assist a medical practitioner with placement of an endotracheal tube within a subject. Methods for placing an endotracheal tube using a laryngoscope are well known to those of skill in the art. Thus, any blade structure that can be used to assist placement of a tube into the airways of the subject can be used. For example, Miller and Macintosh blades and sheaths for these respective blades can be used.

In a further aspect, the blade can be made of any appropriate material including, for example and without limitation, stainless steel. Other materials commonly used for laryngoscope blades can also be used including those that can be readily sterilized. The materials can exemplarily be rigid or semi-rigid. In a further aspect, the elongated blade portion can have a conventional shape and can be, for example and without limitation, generally straight, at least partially curved, or substantially curved. Of course, it is contemplated that the particular blade configurations can be selected by one of skill in the art based on many factors, including, but not limited to, the preference of the practitioner inserting the endotracheal tube into the subject.

Connections between the blade and the handle 102 are well known to those skilled in the art. In one exemplary aspect, mounting can be accomplished by removably securing the mounting portion 106 of the blade to the bottom portion of the handle 102. Moreover, the laryngoscope can be configured to allow for movement of the blade relative to the handle when mounted. For example, the securable attachment of the mounting portion to the handle can be a hinged to allow for the movement of the elongated portion of the blade along an arc both towards and away from the handle.

In one example, the mounting portion of the blade can be connected to the bottom portion of the handle using an axle mount 112. In this aspect, the axle mount can be mounted to the bottom portion of the handle and is configured such that the mounting portion 106 of the blade can be mounted in a removable fashion to the handle. In a further aspect, the axle mount can be conventionally configured to allow the blade to be moved in an arcuate path from a closed to open position or to any position along the arcuate path. In one aspect, the blade of the described laryngoscope can be selectively movable along an arcuate path between a first position and a second position. In one example, the arcuate path of the blade can be in a plane that substantially bisects a longitudinal axis of the handle. It is contemplated that the blade can be selectively positionable at any point along its arcuate path between the respective first and second positions. Such movement and the use of such an exemplary axle mount is known to those skilled in the art of laryngoscope manufacture and use.

In one aspect, the mounting portion of the blade can comprise side walls 302 that have an exterior surface. In another aspect, at least one of the side walls can define at least one aperture 304 that extends through the wall. Preferably, the mounting portion 106 of the blade can comprise two generally parallel side walls 302. In this aspect, each side wall can have a predetermined thickness and a longitudinal axis that is substantially parallel to the longitudinal axis of the blade in its first position.

In a further aspect of the invention, the laryngoscope can comprise an actuator system comprising at least one latching pin 306. The actuator system can further comprise a means for selectively driving the latching pins about and between an extended position and a retracted position. For example and without limitation, the means for selectively driving the latching pins can comprise a motor or solenoid. In one aspect, at least a portion of the actuator system can be disposed in an interior portion of the mounting portion of the blade.

In another aspect, the means for selectively driving the latching pins 306 can further comprise a cam 308, a shaft solenoid drive 312, also referred to herein as a solenoid drive shaft, and one or more linkage armatures 314. In one example, the shaft is a moveable portion of the motor or solenoid that is configured to be selectively driven to rotate about its longitudinal axis. The cam is mounted to a portion of the shaft and can be selectively driven to rotate about the longitudinal axis of the shaft. In one aspect, each linkage armatures is configured to be operatively coupled to a portion of the nose of the cam. Optionally, the cam can have a pair of noses and each linkage armatures is operatively coupled to one individual nose. In this aspect, it is further contemplated that the noses would be positioned generally along a common axis of the cam. In one aspect, the common axis of the cam can form the largest cross-sectional length dimension of the cam.

In a further aspect, the actuator system can further comprise a solenoid or motor 310, as well as at least one pin mount 316. Optionally, one skilled in the art will appreciate that any combination of motor and intermediate member or members linking the motor's generated force to the pins for the pins extension or retraction is contemplated to be an actuator system.

Thus, the disposable sleeve laryngoscope can comprise a handle portion, a blade portion, including mounting portion, an elongated blade portion and an actuator system. The actuator system can be disposed at least partially within the mounting portion. The actuator system can be driven electrically and selectively by a user for the selective securement or removal of the disposable sleeve.

Each latching pin can be configured to pass through an aperture of the mounting portion. The actuator system can be configured to selectively move between an extended position that is configured to selectively secure the disposable blade cover over at least a portion of the elongated portion of the blade, in which each latching pin extends through one aperture and outwardly away from the exterior surface of the side wall, and a retracted position configured to allow for the selective removal of the blade cover from the elongated portion of the blade, in which each latching pin is retracted within the aperture and below the plane of the exterior surface of the side wall.

The disposable sleeve can be securably attached to the exemplary laryngoscope 100. Securable attachment may be desirable during procedures for which the laryngoscope is used, including assisting the insertion of an endotracheal tube into the subject. In one aspect the disposable sleeve remains securely attached to the laryngoscope during a procedure. Upon completion of the medical procedure, the disposable sleeve can be selectively removed by unsecuring the disposable sleeve from the laryngoscope before removal.

In one exemplary embodiment, the disposable sleeve can be securably attached to the laryngoscope in a position covering at least a portion of the elongated portion of the blade by protruding members or latching pins. Exemplary latching pins 306 are shown in FIGS. 3-8.

Figure 2:
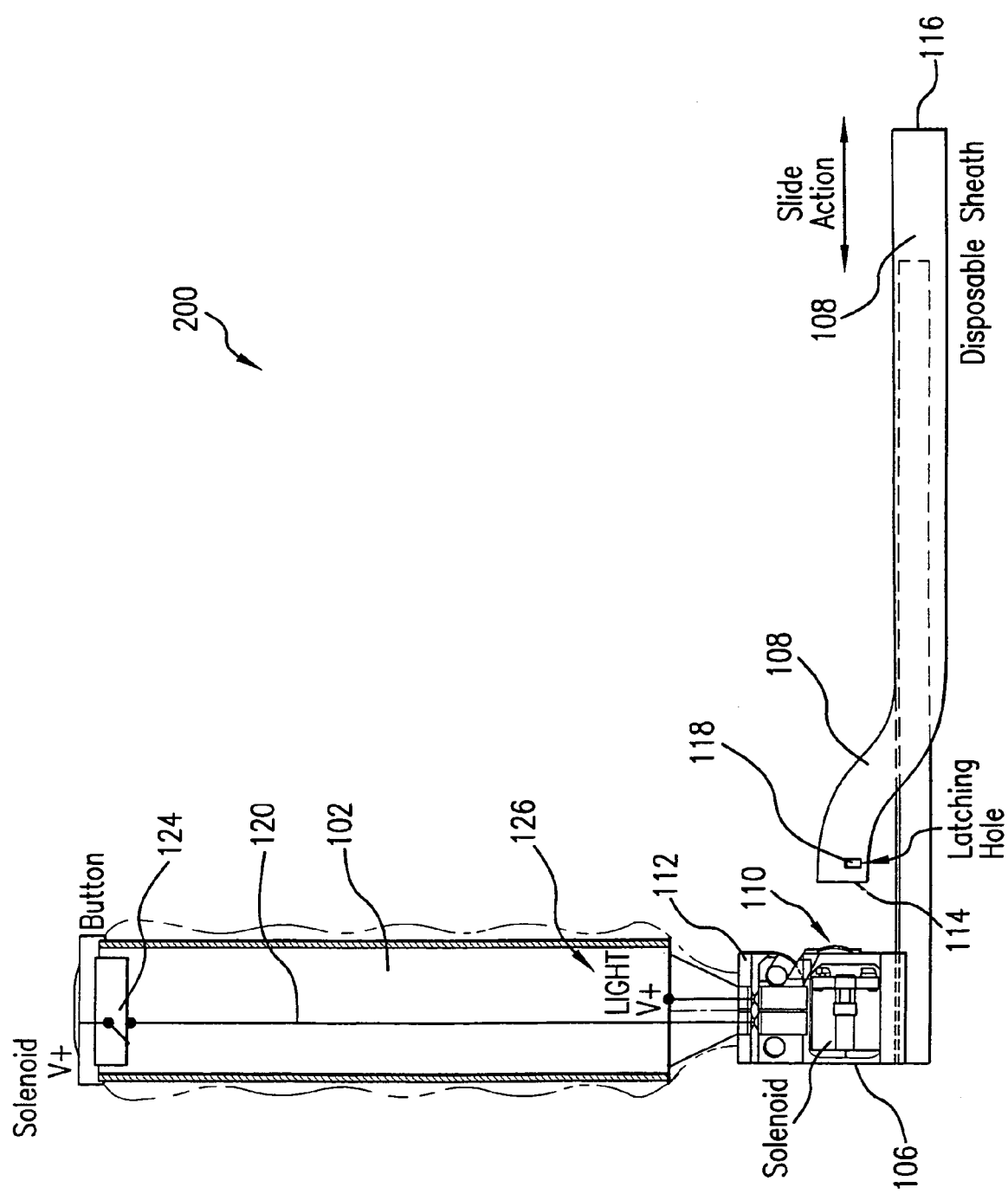
FIG. 2 is a schematic side elevational view of a second embodiment of the laryngoscope and disposable blade cover of the present invention.

FIG. 3 shows an exploded schematic diagram of an exemplary embodiment of a disposable sleeve laryngoscope similar to those described in FIGS. 1 and 2. FIG. 3 shows the mounting portion 106 in greater detail. As described above, each side wall 302 can have at least one aperture 304 located therethrough the wall. The apertures are designed for the ingress and egress of a complementary pin 306. Thus, the number of pins 306, holes 118, and apertures 304 can vary. For example, an exemplary embodiment can have at least one pin, hole, and aperture. Typically, the number of apertures in the side walls, the number of latching pins and the number of cavities or holes in the disposable sleeve will be the same. As described above, there can also be a plurality, and typically, although not required, the number of each hole, aperture and pin will be equal.

Apertures 304 are configured such that pins or protrusions for engagement with the disposable sleeve can be extended therethrough the apertures 304 for engagement with the latching holes 118 of a disposable sleeve 114 or for retraction therethrough of the pins from the holes 118 and into the interior of mounting portion 106.

The latching pins 306 in the retracted position can be enclosed or partially enclosed within the interior of mounting portion. At least a portion of the pins can also be located within the aperture. The pins can be extended through the side walls upon activation of the motorized mechanism.

Each latching pin can be configured to pass through one aperture of the mounting portion and therein at least a portion of one cavity of the sheath to selectively secure the sheath to the blade. The actuator system can also be configured to selectively move between an extended position, in which each latching pin extends through one aperture and outwardly away from the exterior surface of the side wall, and a retracted position, in which each latching pin is retracted within the aperture and below the plane of the exterior surface of the side wall. The sheath can be configured to selectively cover at least a portion of the elongated portion of the blade. When the actuator system is in the retracted position, the sheath can be selectively and slideably removed from the elongated portion of the blade.

Latching pins 308 can project from within the interior of the mounting portion of the blade. The pins 308 can be seated into complimentary holes or cavities 118 (FIGS. 1 and 2) within the proximal end of the removable blade cover 114. When seated, the protrusions or pins help to securably attach the disposable sleeve onto the laryngoscope.

In one aspect, the pins or protrusions can exist in an extended position wherein the pins 308 are seated in the holes 118 or cavities in the disposable sleeve 114. In this position, the disposable sleeve is secured in its covering position.

The pins 308 can also be selectively moved from the extended position to a retracted position. In the retracted position, the pins 308 are withdrawn from their seated position within the holes 118 in the disposable sleeve 114. When the pins are withdrawn from the holes in the sleeve, they no longer function to securably attach the disposable sleeve to the laryngoscope and the sleeve can be selectively removed from the laryngoscope for disposal.

The pins or protrusions 306 can be selectively placed into a position protruding into the cavities or holes 118 or into a position retracted from the holes 118. In one aspect, the selective movement between the retracted position and the extended position can be accomplished by a motorized mechanism. In operation, a user may selectively activate the motor to move the pins between their extended or retracted position. The user may also activate the motor to move the pins between their retracted and extended position. Thus, the operator can selectively activate the motor to cause it to either move the pins from their retracted position to their extended position for securing the disposable sleeve about the laryngoscope, or to move the pins from the extended position to the retracted position for removal of the blade from about the laryngoscope.

Activation of a motor 310 (FIG. 3) can be accomplished by a user of the laryngoscope by engaging a circuit 120 (FIG. 1). The circuit 120 can be engaged by any conventional switching mechanism that allows for the user to selectively engage the circuit. For example, and without limitation, the switching mechanism can be a button, switch or other mechanism used to engage the electrical circuit to provide electrical power to the motor 310 for operation thereof. Thus, the user can engage the circuit to selectively activate the motor to drive movement of the pins 306 between their extended or retracted position.

Optionally, in some exemplary embodiments, there can be multiple latching holes or cavities 118 in the disposable sleeve 108. Complimentary with the multiple holes, there can be multiple protrusions or latching pins 306 that can engage or be removed from the multiple holes. In other exemplary embodiments, there can be one pin 306 with one complementary hole 118. Therefore, it is contemplated that there can be at least one latching hole 118 in the disposable sleeve and at least one complimentary latching pin or protrusion 306 for selective engagement of the hole.

Figure 4:
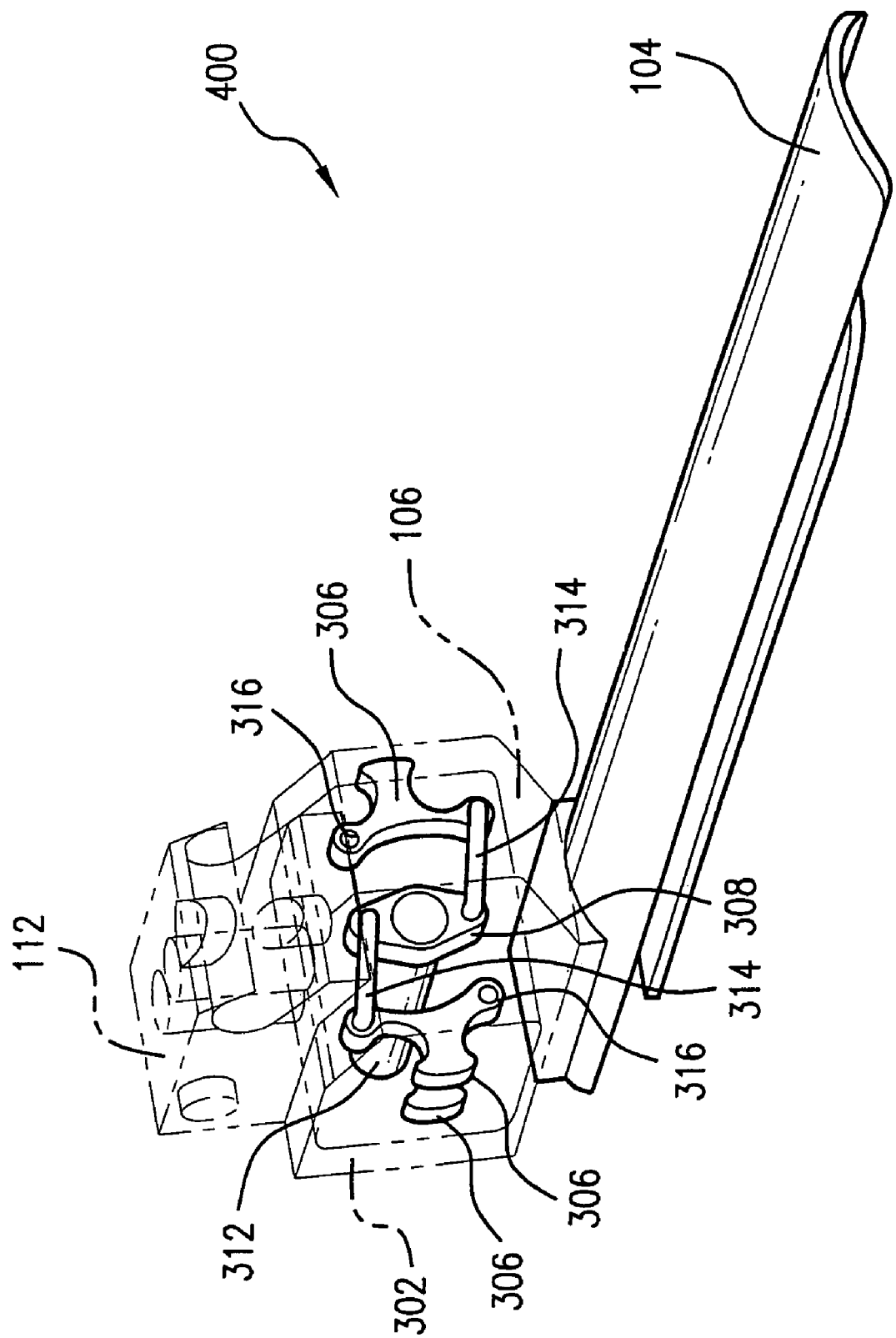
FIG. 4 is a perspective view of an elongated portion, a mounting portion, and an axle mount of the laryngoscope of FIG. 1.

FIG. 2 shows an exemplary embodiment of the disposable sleeve laryngoscope 200 wherein the sleeve has one latching hole 118. In the embodiment shown in FIG. 2, there can also be a second hole 118 opposite of the shown hole 306. In this case, the sleeve can comprise two holes and the laryngoscope can comprise two complementary pins 306. Any combination in number of pins and complementary holes can be used to selectively secure the sleeve about the laryngoscope. In another example, FIG. 4 shows a schematic diagram of the elongated and mounting portions of the blade in an exemplary operative configuration. In this example, the embodied operative configuration 400 has two latching pins 306 shown in their extended position through a sidewall 302 of the mounting portion.

The latching pins 306 are operatively connected to the sol cam 308 by linkage armatures 314. This configuration allows for the transfer of force from a solenoid to cause rotational clockwise or counterclockwise motion of the sol cam. Motion of the sol cam can transfer force through the linkage armatures 314 to the pins 306, which are configured for pivotal movement around the pin mount 316, for extension or retraction. In the retracted position the pins 306 can be flush with the side walls. It is not intended, however, that the pins 306 necessarily attain a flush position relative to the side walls. Rather, the pins only need to be withdrawn out of the holes 118 in the disposable sleeve to an extent that the disposable sleeve can be selectively removed.

As shown in the exemplary embodiment, clockwise movement can encourage retraction of the latching pins 306. In this position the sleeve 114 is no longer securably attached about the laryngoscope. Similarly, a counterclockwise rotation of the sol cam can produce a movement of the pins into their extended position for engagement with the holes 118 in the disposable sleeve. To move the linkage cam 314 in a clockwise or counterclockwise direction, the linkage cam can be operatively attached to a motor mechanism or solenoid 310 through a shaft or solenoid drive shaft 312 that engages the sol cam 308 and that also engages with the solenoid or motor such that the motor can drive rotation of the solenoid shaft 312 in a clockwise or counterclockwise fashion causing a complimentary clockwise or counterclockwise rotation of the sol cam.

Figure 5:
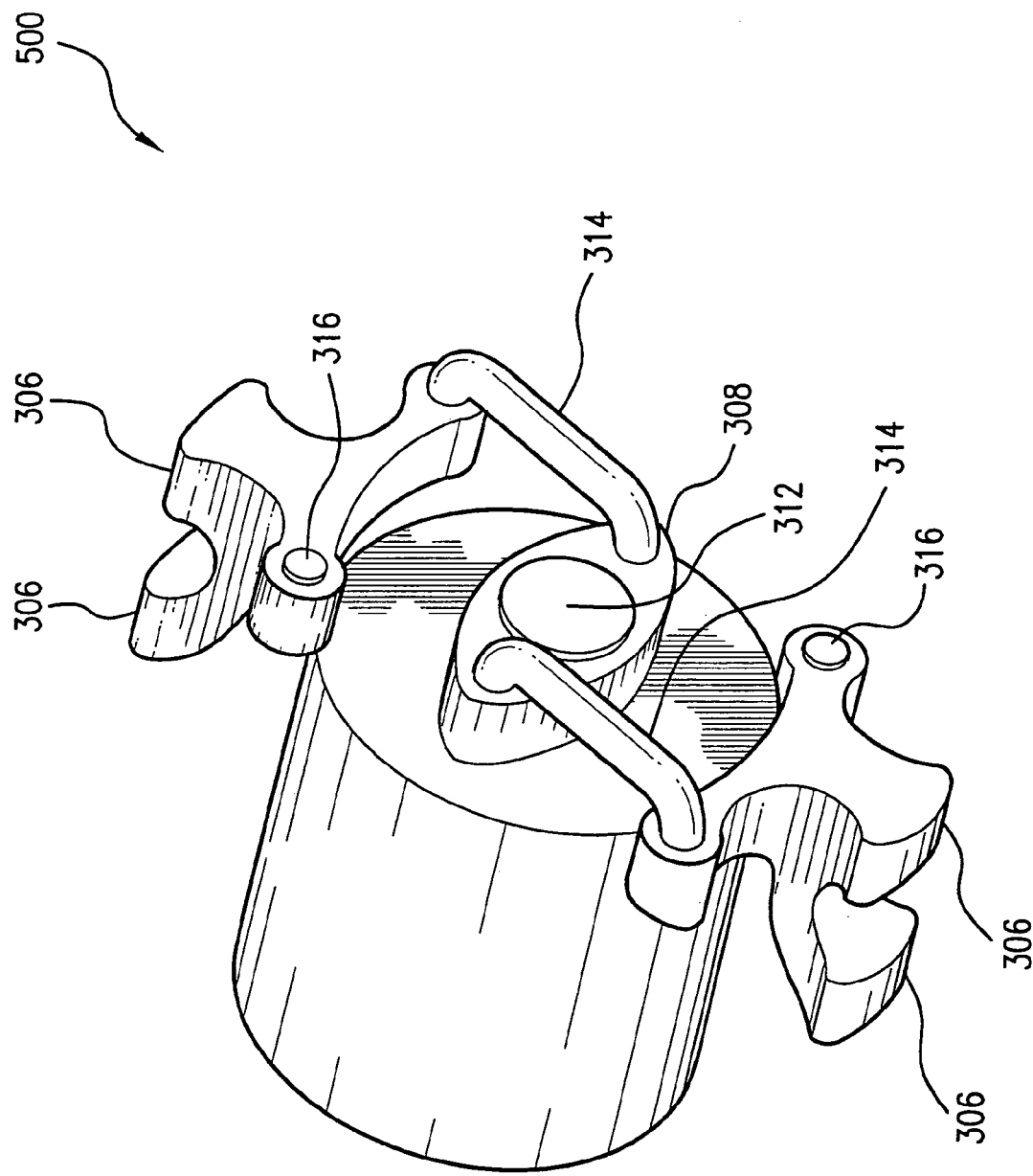
FIG. 5 is a perspective view of an embodiment of an actuator system of the exemplary laryngoscope that comprises at least one latching pin, and showing a means for selectively driving the latching pins about and between an extended position and a retracted position.
Figure 6:
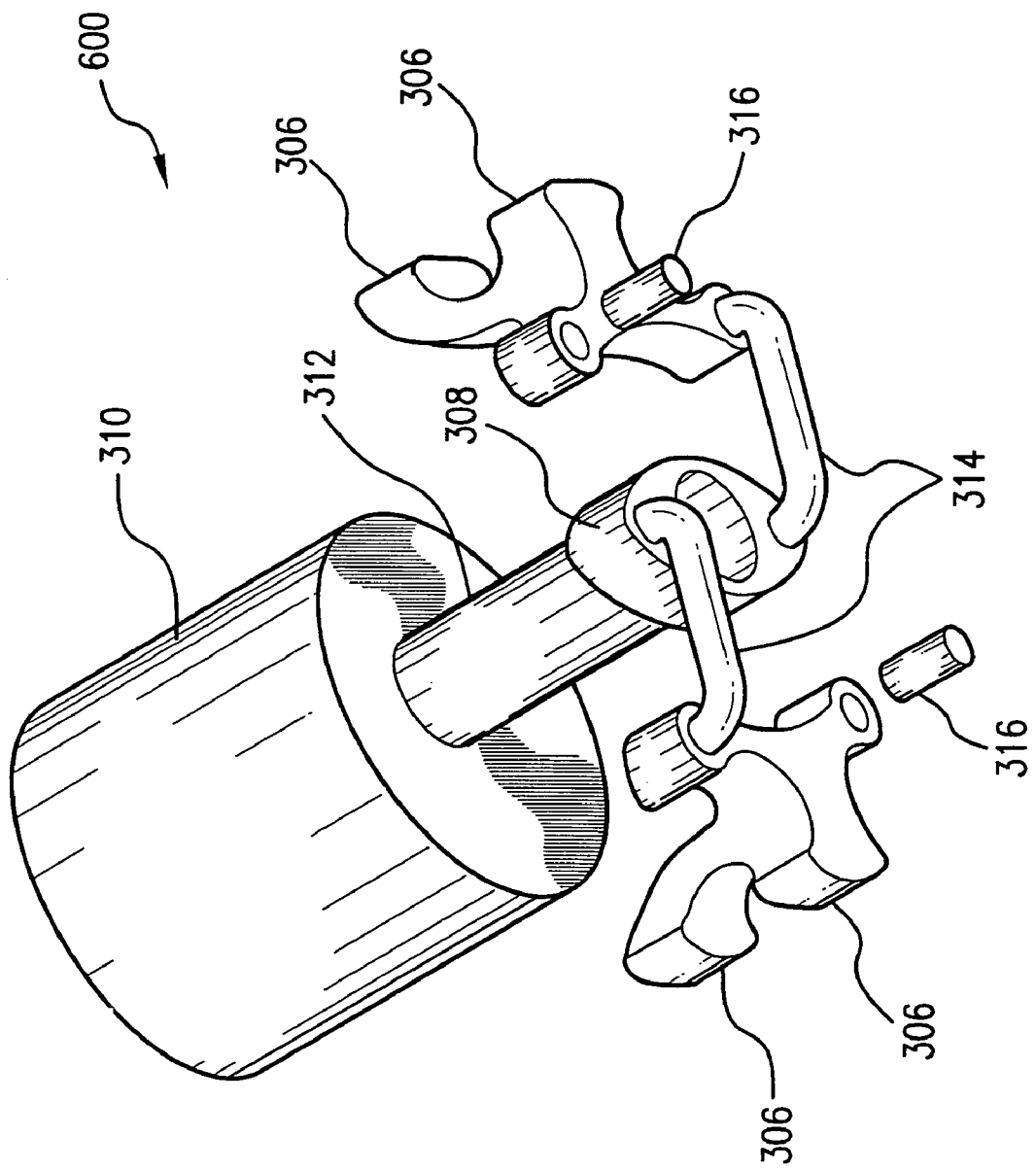
FIG. 6 is an exploded perspective view of the means for selectively driving the latching pins about and between an extended position and a retracted position of FIG. 5.

FIGS. 5 and 6 show an exemplary actuator system for use with an exemplary disposable sleeve laryngoscope. This view shows an exemplary embodiment with two latching pins 306 on each side for a total of four latching pins. A disposable sleeve for use with this embodiment can comprise four complimentary latching holes. The actuator system can be disposed with the interior of a mounting portion 106 and the mounting portion can have complimentary apertures for ingress and egress of the four latching pins 306.

FIG. 5 also shows the linkage armatures 314 for transferring rotational movement of the sol cam 308 to the latching pins 306. Rotational movement can be delivered to the sol cam by the solenoid shaft 312 which can be operatively engaged with the solenoid or motor 310. Thus, activation of the solenoid motor 310 can cause the rotational movement of the shaft 312 in a counterclockwise fashion which causes a complementary clockwise or counterclockwise rotational movement of the solenoid cam. This, in turn, causes a force to be transferred to the linkage armatures 314, which causes either the retraction or extension of the pins 306.

FIG. 6 is an exploded view of the exemplary actuator system 600. In this embodiment, the solenoid 312 or motor which acts on the solenoid drive or shaft 312 is operatively connected to the sol cam 308 for delivering a rotational force generated by the solenoid or motor 310 through the solenoid shaft to the sol cam for rotational movement in a clockwise or counterclockwise fashion of the sol cam. Force is transferred into the linkage armatures and to the pins 306. In this embodiment, the pins 306 are pivotally mounted to the pin mount, which is fixed relative to the mounting portion. Thus, rotational force applied to the sol cam can deliver a force through the linkage armatures to the pins to allow for the selective rotative movement of the pins 306 relative to and about the pin mount 316 such that the force transferred by the linkage armatures causes the outward or inward movement of the pins through the aperture on the sidewall of the mounting portion.

In one aspect, means for selectively driving the latching pins can comprise a cam that is operatively coupled to the at least one latching pin such that selective rotation of the cam causes selective movement of the at least one latching pin between its respective retracted and extended position. The means can further comprise a means for rotating the cam. The means for rotating the cam can comprise a motor having a shaft that is rotatable about its longitudinal axis. In one non-limiting example, the motor can be a solenoid motor.

Figure 7B:
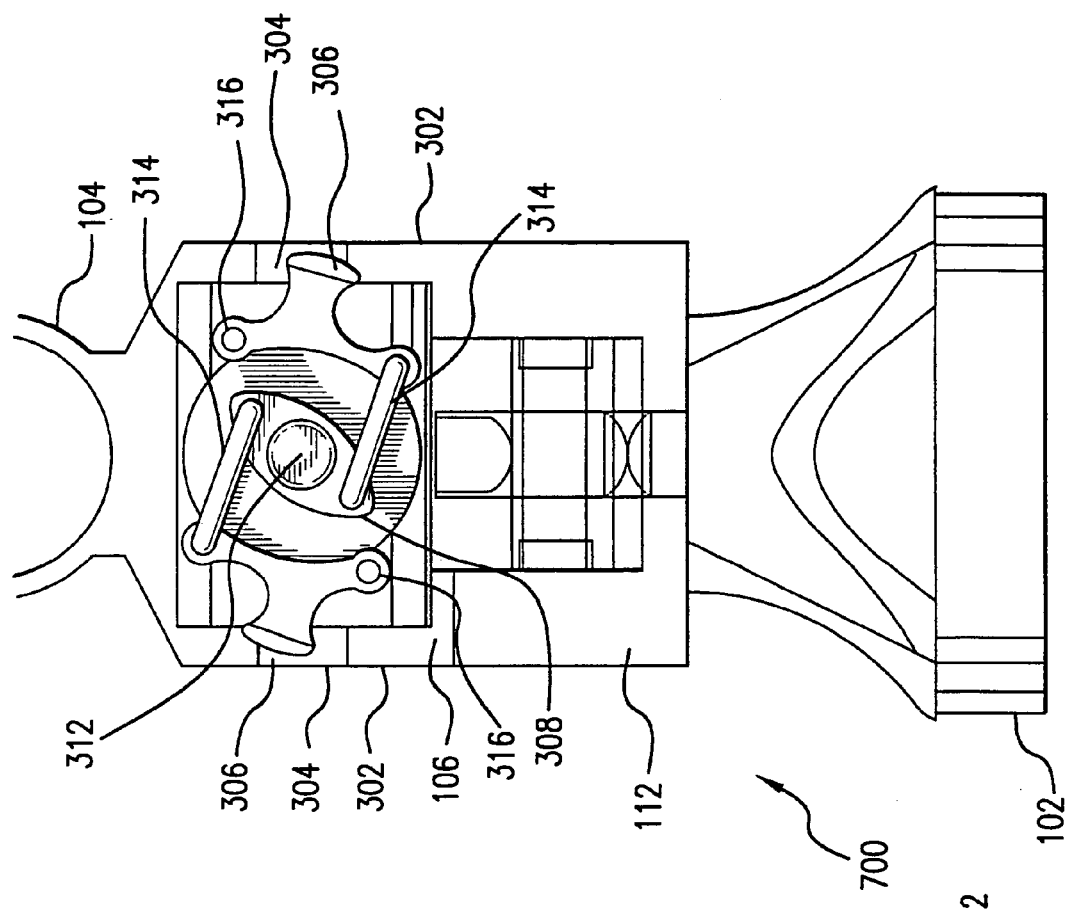
FIG. 7B is a schematic cross-sectional illustration of the laryngoscope of FIG. 1 taken across line 7-7 of FIG. 1, showing the pair of latching pins in an extended position.
Figure 7A:
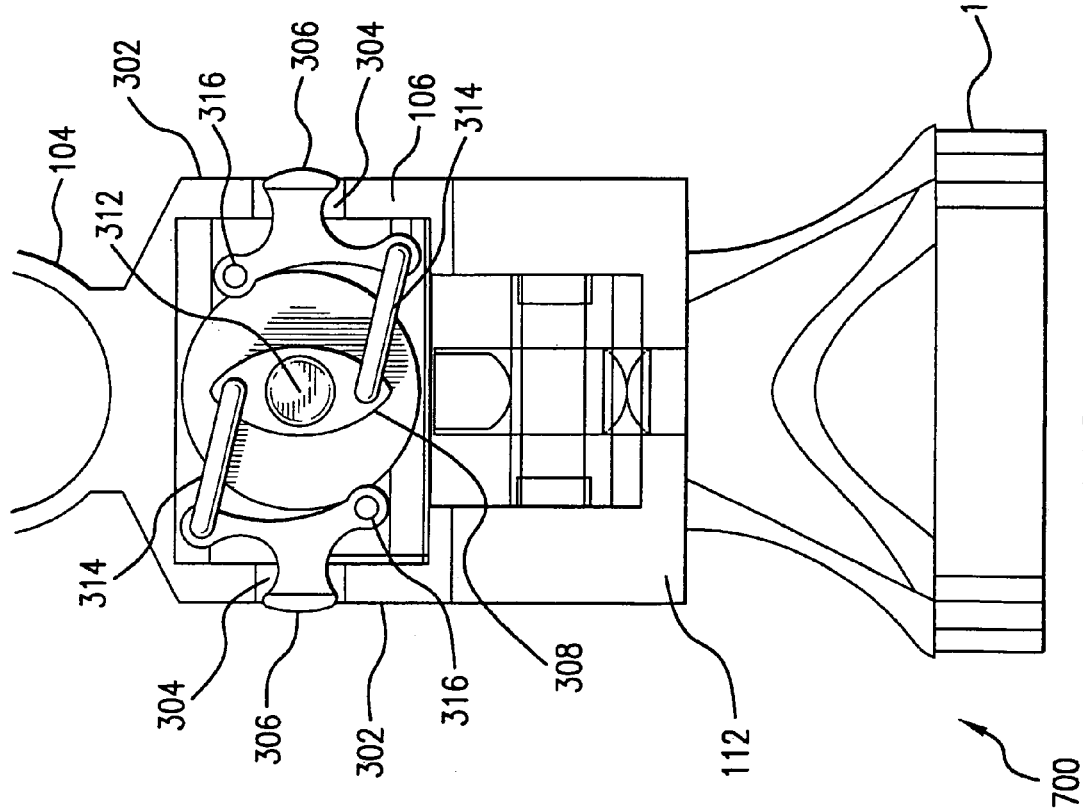
FIG. 7A is a schematic cross-sectional illustration of the laryngoscope of FIG. 1 taken across line 7-7 of FIG. 1, showing a pair of latching pins in a retracted position.

FIG. 7A shows a cross-section through plane along the line A shown in FIG. 1 and shows the actuator system positioned when the latching pins 306 are in their extended position. In this position, the pins can engage a disposable sleeve so that it could be securably attached to the laryngoscope. FIG. 7B shows a cross-section of the blade through the same plane A shown in FIG. 1 and shows the latching pins in their retracted position. As is shown in FIG. 7B, clockwise rotation of the sol cam 314 caused by force from the sol shaft 312 and the solenoid 310 causes a rotational movement of the sol cam. In the shown embodiment, clockwise movement of the sol cam places a pulling force on the linkage armatures 314 to withdraw the pins 306 through the apertures 304 to subsequently position the pins 306 into their retracted position. One would appreciate that movement of the sol cam in the opposing direction can produce a pushing type force on the linkage armatures such that the pins are extended into the position shown in FIG. 7A. In this position, the pins extend beyond flush with the sidewalls of the mounting portion 302 such that they can engage complimentary holes 118 on a disposable sleeve 114. Whether a clockwise or counterclockwise motion of the solenoid is used to drive the solenoid cam and in turn to remove, to retract or to extend said pins is a design choice well within the skill in the art. Thus, a counterclockwise motion can retract the pins or a counterclockwise movement can extend the pins. Similarly, a clockwise rotational movement can extend the pins or a clockwise rotation can withdraw the pins.

FIG. 8 shows another exemplary embodiment of an actuator system that can be used in a disposable sleeve laryngoscope of the present invention. In this embodiment, the actuator system is used without a rotationally driven actuator mechanism. In such a system, shown in FIGS. 8A and 8B, the latching pins 306 can positioned in an extended position (FIG. 8A) or a retracted position (FIG. 8B). A force can be transferred to the pins for selective extension of the pins through the apertures 304 in the sidewalls 302. The force can be transferred to the pins through a pair of opposed armatures 802 that have an angular intermediate portion 803. In one aspect, a distal end portion of the armatures 802 is securably attached to the bottom end of the pins 306. In one aspect, the pins are selectively translated from the extended position to the retracted position by applying force to a pushing member 804 which translates along a substantially linear path toward the pins and acts on the angularly disposed portions of the opposing armatures to move the opposing armature inward and toward each other. As exemplarily shown in FIGS. 8A and 8B, the movement of the pushing member 804 towards the pins causes the intermediate portion 803 of the opposed armatures 802 to be driven from a position more lateral to the sidewalls 302 to a position more medial to the central axis of the mounting portion. The medial position of the intermediate portion 803 causes a complimentary retraction of the pins 306 through the apertures 304. As one would appreciate, lateral movement of the intermediate portions of the opposed armatures 802 from the medial position towards a more lateral position in proximity to the lateral walls 302 allows for the extension of the pins into their extended position.

In this embodiment, the pushing and retraction of the pushing member to allow for the medial or lateral movement of the intermediate portions of the opposed armatures can be accomplished through manual force applied to or removed from the activator 806. The manual force can also be applied through automated or semi-automated means such as a motor.

Thus, the invention described and claimed herein is a laryngoscope or laryngoscope system comprising a handle, a blade and an actuator system. The actuator system can comprise at least one latching pin for securably attaching a disposable sleeve 114. The pins can be positioned and moved between an extended or retracted position. Extension of the pins and retraction of the pins can be accomplished in a variety of ways, several of which are described herein. For example, as described above, in one embodiment a motorized or otherwise driven rotational force can deliver energy for extension or retraction of the pins as shown in FIGS. 1-7. Moreover, a force causing medial or lateral movement of the pins that does not use a rotational force can be used as described in the exemplary embodiment shown in FIG. 8. Thus, the means for retracting and extending the pins are not intended to be limiting.

Also provided herein is a laryngoscope for use with a disposable blade cover, comprising a handle and a blade. The blade can have an elongated portion and a mounting portion. The mounting portion can be configured to position the elongated portion relative to the handle. The mounting portion can comprise side walls having an exterior surface. At least one of the side walls can define at least one aperture extending therethrough the wall. The laryngoscope can further comprise at least one latching pin. Each latching pin can be configured to pass through one aperture of the mounting portion to selectively move between an extended position and a retracted position. In the extended position, each latching pin can extend through one aperture and outwardly away from the exterior surface of the side wall to selectively secure the disposable blade cover over at least a portion of the elongated portion of the blade. In the retracted position, each latching pin can be retracted within the aperture and below the plane of the exterior surface of the side wall configured to allow for the selective removal of the blade cover from the elongated portion of the blade.

As described above, removal of the disposable sleeve can be accomplished manually. For example, a medical practitioner can pull the disposable sleeve distally along the elongated portion of the blade until it is fully removed from its position covering the blade. Removal of the disposable sleeve cover can also be assisted or accomplished using non-manual means. In one aspect, an ejector mechanism can be positioned on the mounting portion that is configured to eject the disposable blade cover away from the mounting portion and along the length of the elongated portion. For example, the ejector mechanism can comprise a spring member or spring resist 110 that is used to assist or accomplish sleeve removal. In this aspect, the spring member 110 can be positioned such that when the pins are withdrawn from the latching holes that the spring member encourages the sleeve distally along the length of the elongated portion. In one aspect, the spring member can be securably attached to the mounting portion and positioned between the mounting portion and the proximal end of the disposable blade covering. In one aspect, the spring can be held in a compressed configuration between the distal end of the disposable blade cover and the mounting portion when the actuator is in its extended position. In operation, when the actuator is moved to its retracted position the spring can be released to eject the disposable blade cover along the elongated portion of the blade.

In a further aspect, the spring member can be powerful enough to fully eject the disposable blade covering from the elongated portion of the blade or can assist the manual removal by ejecting the disposable sleeve some distance along the elongated portion of the blade.

The preceding description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. The corresponding structures, materials, acts, and equivalents of all means or step plus function elements in the claims below are intended to include any structure, material, or acts for performing the functions in combination with other claimed elements as specifically claimed.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only.

What is claimed is:

1. A laryngoscope, comprising:
a handle;
a blade having an elongated portion and a mounting portion, the mounting portion being configured to position the elongated portion relative to the handle, wherein the mounting portion comprises side walls having an exterior surface, and wherein at least one of the side walls defines at least one aperture extending therethrough the wall;
a disposable blade cover comprising a proximal end and a spaced distal end, wherein at least a portion of the distal end of the disposable blade cover defines at least one cavity configured to slidably receive at least a portion of the elongated portion of the blade, and wherein the proximal end of the disposable blade cover defines at least one latching cavity; and
an actuator system comprising at least one latching pin, each latching pin being configured to pass through one aperture of the mounting portion and be at least partially received by the at least one latching cavity, and wherein the actuator system is configured to selectively move the at least one latching pin between an extended position that is configured to selectively secure the disposable blade cover over at least a portion of the elongated portion of the blade, in which each latching pin extends through one aperture outwardly away from the exterior surface of the side wall and at least partially extends therein the at least one latching cavity, and a retracted position configured to allow for the selective removal of the disposable blade cover from the elongated portion of the blade, in which each latching pin is retracted within the aperture and below a plane of the exterior surface of the side wall.

2. The laryngoscope of claim 1, further comprising an ejector mechanism positioned on the mounting portion and configured to eject the disposable blade cover away from the mounting portion and along the length of the elongated portion.

3. The laryngoscope of claim 2, wherein the ejector mechanism comprises a spring securably attached to the mounting portion and positioned between the mounting portion and the proximal end of the disposable blade cover.

4. The laryngoscope of claim 3, wherein the spring is held in compression between a distal end of the disposable blade cover and the mounting portion when the at least one latching pin is in the extended position, and wherein the spring is released when the at least one latching pin is in the retracted position to eject the disposable blade cover along the elongated portion of the blade.

5. The laryngoscope of claim 1, wherein the blade is selectively movable relative to the handle in an arc between a first position and a second position.

6. The laryngoscope of claim 5, wherein the blade moves in a plane that bisects a longitudinal axis of the handle.

7. The laryngoscope of claim 6, wherein the blade is selectively positionable at any point along the arc between the first and second positions.

8. The laryngoscope of claim 5, wherein the mounting portion is positionable between the handle and the elongated portion of the blade.

9. The laryngoscope of claim 8, wherein the side walls of the mounting portion comprise two generally parallel side walls, and wherein each side wall has a predetermined thickness and a longitudinal axis that is substantially parallel to the longitudinal axis of the blade in its first position.

10. The laryngoscope of claim 1, wherein the actuator system comprises a means for selectively driving the at least one latching pin.

11. The laryngoscope of claim 10, wherein the means for selectively driving the at least one latching pin comprises:
a cam that is operatively coupled to the at least one latching pin such that selective rotation of the cam causes selective movement of the at least one latching pin between its respective retracted position and extended position; and
a means for rotating the cam.

12. The laryngoscope of claim 11, wherein the means for rotating the cam comprises a motor having a shaft that is rotatable about its longitudinal axis.

13. The laryngoscope of claim 12, wherein the motor is a solenoid motor.

14. The laryngoscope of claim 1, wherein at least a portion of the actuator system is disposed therein an interior portion of the mounting portion of the blade.

15. A laryngoscope, comprising:
a handle;
a blade having an elongated portion and a mounting portion, the mounting portion being configured to position the elongated portion relative to the handle, wherein the mounting portion comprises side walls having an exterior surface, and wherein at least one of the side walls defines at least one aperture extending therethrough the wall;
a disposable blade cover comprising a proximal end and a spaced distal end, wherein at least a portion of the distal end of the disposable blade cover defines at least one cavity configured to slidably receive at least a portion of the elongated portion of the blade, and wherein the proximal end of the disposable blade cover defines at least one latching cavity; and
at least one latching pin, each latching pin being configured to pass through one aperture of the mounting portion and be at least partially received by the at least one latching cavity and to selectively move between an extended position in which each latching pin extends through one aperture outwardly away from the exterior surface of the side wall and at least partially extends therein the at least one latching cavity to selectively secure the disposable blade cover over at least a portion of the elongated portion of the blade and a retracted position in which each latching pin is retracted within the aperture and below a plane of the exterior surface of the side wall configured to allow for the selective removal of the disposable blade cover from the elongated portion of the blade.

16. A laryngoscope, comprising:
a handle;
a blade having an elongated portion and a mounting portion, wherein the mounting portion is configured to position the elongated portion relative to the handle, wherein the mounting portion comprises side walls having an exterior surface, and wherein at least one of the side walls defines at least one aperture extending therethrough the wall;
a disposable blade cover comprising a proximal end and a spaced distal end, wherein at least a portion of the distal end of the disposable blade cover defines at least one cavity configured to slidably receive at least a portion of the elongated portion of the blade, and wherein the proximal end of the disposable blade cover defines at least one latching cavity;
at least one latching pin, each latching pin being configured to pass through one aperture of the mounting portion and be at least partially received by the at least one latching cavity and to selectively move between an extended position in which each latching pin extends through one aperture and outwardly away from the exterior surface of the side wall and at least partially extends therein the at least one latching cavity to selectively secure the disposable blade cover over at least a portion of the elongated portion of the blade and a retracted position in which each latching pin is retracted within the aperture and below a plane of the exterior surface of the side wall configured to allow for the selective removal of the disposable blade cover from the elongated portion of the blade; and
means for selectively driving the at least one latching pin between the extended and retracted positions.

* * * * *